United States Patent [19]

Vashi

[11] Patent Number: 5,374,187
[45] Date of Patent: Dec. 20, 1994

[54] ORTHODONTIC APPLIANCE

[76] Inventor: Nikhil S. Vashi, Neelkanth, 15-A Unik Society, Behind Pratap Society, J. P. Road, Andheri (W) Bombay-400053, India

[21] Appl. No.: 146,740

[22] Filed: Nov. 2, 1993

[51] Int. Cl.$^5$ ................................. A61C 3/00
[52] U.S. Cl. .......................... 433/8; 433/10; 433/17; 433/24
[58] Field of Search ............ 433/8, 9, 10, 16, 17, 433/24

[56] References Cited

U.S. PATENT DOCUMENTS

| | | | |
|---|---|---|---|
| 3,163,933 | 1/1965 | Begg | 433/14 |
| 3,660,900 | 5/1972 | Andrews | 433/24 X |
| 4,242,085 | 12/1980 | Wallshein | 433/16 X |
| 4,427,381 | 1/1984 | Hall | 433/14 |
| 4,496,318 | 1/1985 | Connelly | 433/14 |
| 4,531,911 | 7/1985 | Creekmore | 433/8 |
| 4,936,774 | 6/1990 | Stoller et al. | 433/17 X |
| 5,037,297 | 8/1991 | Lerner | 433/14 |
| 5,094,614 | 3/1992 | Wildman | 433/14 |
| 5,125,832 | 6/1992 | Kesling | 433/8 |
| 5,129,821 | 7/1992 | Schuetz | 433/8 |
| 5,151,028 | 9/1992 | Snead | 433/17 |
| 5,238,402 | 8/1993 | Rohlcke et al. | 433/8 X |
| 5,248,257 | 9/1993 | Cannon | 433/24 X |
| 5,288,229 | 2/1994 | Huff et al. | 433/17 |

Primary Examiner—Paul J. Hirsch
Assistant Examiner—Nicholas D. Lucchesi

[57] ABSTRACT

This invention relates to an orthodontic appliance comprising of a plurality of brackets and molar tubes for the correction of malocclusion of teeth. The bracket features a horizontal rectangular slot in the gingival surface for securing round arch wires and rectangular arch wires in ribbon-arch mode. The bracket allows free tipping, controlled tipping or bodily movement of the tooth depending on the mode of securing the arch wire to the slot. The molar tube features at least one rectangular tube which is vertical in cross-section, corresponding to the arch wire slot of the bracket. The tube provides better control over the molar tooth leading to stronger anchorage. The appliance allows different tooth movements with total control for precise positioning of all the teeth.

7 Claims, 3 Drawing Sheets

ORTHODONTIC APPLIANCE

This invention relates to an orthodontic appliance comprising of a plurality of brackets and molar tubes for the correction of malocclusion of teeth. This appliance advantageously allows different tooth movements.

BACKGROUND OF THE INVENTION

Any fixed orthodontic appliance consists of a plurality of brackets, molar tubes, arch wires, and orthodontic auxiliaries. One bracket or one molar tube is needed for an individual tooth for engaging the arch wires. A bracket is a block having a contoured surface called a base, matching with the tooth contour and a body having slots for engaging arch wires, lock-pins, ligature wires, and hooks for engaging elastics.

The brackets are attached to the central and the lateral incisors, the canines and the first and the second premolars in the upper and the lower dental arches by means of metal bands or are directly bonded with adhesives.

A molar attachment is a block having a base matching with the tooth contour and one or more round and/or rectangular tubes. The molar attachment is usually referred to as a molar tube. The molar tubes are attached to the first and the second molars in the upper and the lower dental arches by means of metal bands or are directly bonded to the teeth with adhesives.

Various types of arch wires are used which pass through the molar tubes and the arch wire slots in the brackets. The arch wires and various types of elastics engaged to the hooks on the brackets, the molar tubes, and the arch wires exert pressure which move the teeth in the jaw bones for correcting their irregularities.

The conventional fixed appliances can be categorized as i. The Edgewise Appliance and its modifications, mainly the Straight Wire Appliance and the Tip-Edge Appliance;
ii. The Begg Appliance; and
iii. The combination appliances.

In the existing Edgewise Appliance the bracket has a single horizontal rectangular slot on the labial/buccal surface or the face of the bracket for engaging arch wires and the molar tube is horizontal, and rectangular in cross-section. Normally two tubes, one rectangular and one round for a headgear, are used for the first molars in the Edgewise Appliance. The headgear is used for an additional anchorage by means of an extraoral force or for orthopedic correction of the jaw bones. It consists of a facebow and a head or neck strap. The inner bow of the facebow fits into the round tube.

The arch wires have to be bent precisely in all three planes of space to set the teeth in the desired positions. This takes up a lot of clinical time of the orthodontist and so the brackets and the molar tubes were modified.

The Straight Wire Appliance is a modification of the Edgewise Appliance which comprises of preadjusted brackets and molar tubes. The horizontal slot in the face of the bracket is placed at an angle with the base of the bracket called the torque angle. The horizontal slot is also placed at an angle with the long axis of the tooth called the tip angle. The thickness of the base of the bracket varies for an individual tooth. The molar tube is also angulated in the vertical as well as in the horizontal directions. All these modifications minimize the need for bends in the arch wires to place the teeth in their ideal positions. The tip angle, the torque angle, and the thickness of the base of each of the brackets vary as the shapes, sizes, and inclinations of the teeth are different.

The Edgewise Appliance and its modifications have the following disadvantages:
1. The brackets have horizontal slots which do not allow free tipping of the teeth in clockwise and anticlockwise directions during retraction of the teeth;
2. The teeth move bodily which requires heavy forces causing severe discomfort and pain to the patient; and
3. The anchorage has to be reinforced by means of a headgear requiring more cooperation from the patient. Moreover the headgear can cause soft tissue injuries.

The Tip-Edge bracket is another modification of the edgewise bracket. (U.S. Pat. No. 5,125,832). The bracket used in Tip-Edge Appliance has a vertical slot through the body of the bracket for uprighting springs and a rectangular horizontal slot in the face of the bracket for engaging arch wires. The horizontal arch wire slot of the bracket is cut in such a manner that it allows limited tipping of the tooth in one direction only. The molar tube is horizontal, and rectangular in cross-section such that the width is more than the height.

The disadvantages of the Tip-Edge Appliance are:
1. The bracket does not allow the tooth to tip more if needed;
2. Uprighting springs are needed and sometimes even torquing springs are also needed; and
3. It comprises of a bracket which allows limited tipping of teeth in one direction only.

The bracket used in the Begg Appliance has a horizontal slot in the gingival surface of the bracket for the arch wires, a vertical slot through the body of the bracket for lock-pins, uprighting springs, and derotating springs, and a base conforming to the contour of the tooth surface. The molar tube used in the Begg Appliance is horizontal, and round in cross-section. Only round arch wires are used with the Begg Appliance during the treatment. The teeth are positioned in their desired places with the help of the main arch wires and auxiliary springs.

The disadvantages of the Begg Appliance are as follows:
1. Since the bracket is narrow and has a slot in the gingival surface it allows uncontrolled tipping of the teeth and the rotation control is inadequate;
2. The tooth movements are not self-limiting;
3. Since the diameter of the molar tube is much larger than that of the arch wire used there is a tendency for the arch wire to roll in the tube resulting in an inadequate molar control and loss of anchorage;
4. The positioning of the teeth is not as precise as that obtained with rectangular arch wires because rectangular arch wires are not used with the Begg Appliance;
5. It requires uprighting and torquing auxiliaries for positioning of the roots taking up a considerable chairside time since additional wire bending is needed;
6. Due to the particular design of the brackets and the molar tubes of the Begg Appliance, there is a tendency for the upper molars to flare distobuccally during the last stage of the treatment procedure when torquing and uprighting springs are placed for the final settlement of the teeth; and 7. It is difficult to move the posterior teeth mesially as the anterior teeth cannot provide adequate anchorage due to the bracket design.

The combination appliances were developed to eliminate the drawbacks of the Edgewise, the modified Edgewise and the Begg Appliances.

The brackets used in the Combined Anchorage Technique (CAT) and other combination appliances (U.S. Pat. Nos. 5,037,297; 4,496,318; 4,427,381; 3,163,933) have two rectangular slots for the arch wires, one horizontal in the gingival surface of the bracket and the other horizontal in the face of the bracket. One vertical slot through the body is used for uprighting springs, and for lock-pins and ligature wires which secure the arch wire to the horizontal arch wire slot in the gingival surface as in the Begg Appliance. The arch wires used are round for the initial tooth movements and are engaged to the horizontal slots in the gingival surface of the brackets. The precise positioning of the teeth is brought about by rectangular arch wires engaged to the rectangular slots as in the Edgewise Appliance and its modifications.

The disadvantages of the combination appliances are:
1. The brackets are bulky;
2. Tipping cannot be controlled as with the Begg Appliance; and
3. Uprighting springs have to be used.

OBJECTS AND ADVANTAGES

The object of the present invention is to provide an orthodontic appliance comprising of a plurality of brackets and molar tubes to correct malocclusion of teeth in the most efficient and effective manner giving the best possible results with maximum comfort to the patient and with minimum trouble to the orthodontist. This is possible by means of the brackets and the molar tubes as described in this specification.

Accordingly, several objects and advantages of the present invention are:
1. To allow rapid, differential movements of the teeth with better control and less friction using light tipping forces;
2. To allow free tipping, controlled tipping or bodily movement of the teeth in any plane of space as desired by the orthodontist;
3. To provide better anchorage control by allowing tipping of a single tooth or a group of teeth and by bodily movement of the anchor teeth as tipping requires much less force than bodily movement;
4. To allow proper setting of the teeth with three dimensional control over all the teeth using a rectangular arch wire;
5. To allow effective and rapid opening of the bite;
6. To eliminate the use of heavy forces which cause discomfort and pain to the patient;
7. To reduce the need for patient cooperation;
8. To provide facility for the use of a headgear to apply orthopedic forces to the upper jaw to correct jaw discrepancies in a growing patient;
9. To allow better control over the anchor molars;
10. to reduce the chair side time needed by the orthodontist; and
11. to reduce the duration of the treatment.

SUMMARY OF THE INVENTION

The bracket of this invention has a rectangular arch wire slot in the gingival surface which engages a round wire during the initial phase of the treatment and a rectangular arch wire in ribbon-arch mode in the finishing phase of the treatment. The flat surfaces of the rectangular arch wire are in the vertical plane when inserted into the arch wire slot. The arch wire slot in the gingival surface allows free tipping, controlled tipping or bodily movement of the tooth as desired by the orthodontist. The bracket has two vertical slots through the body of the bracket at right angles to the arch wire slot for engaging lock pins, and ligature wires for securing the arch wire to the arch wire slot. There is another horizontal rectangular slot in the incisal surface of the bracket which can be used for an additional arch wire. The bracket provides necessary rotational control throughout the treatment.

The upper first molar attachment has three tubes, one rectangular tube for the main arch wire, one round tube occlusal to the rectangular tube for an additional arch wire and another bigger round tube buccal to the round tube for a headgear. The rectangular molar tube is in ribbon-arch mode i.e., the height is more than the width in cross-section, to correspond to the bracket slots.

The lower first molar attachment has two tubes, one rectangular tube in ribbon-arch mode and one round tube occlusal to the rectangular tube.

The upper and the lower second molar attachments have rectangular tubes only, in ribbon-arch mode.

The rectangular tubes provide better buccolingual control of the anchor molars and the bite opening is rapid and effective.

The round tube on the first molar has to be used for an additional anchorage by means of a round wire which may engage the slot in the incisal surface of the premolar brackets only or it may engage the slot in the incisal surface of all the brackets on the teeth anterior to the molars. These slots are also used for engaging ligature wires, elastic modules, and power chains.

The objects and advantages of the present invention will become apparent from a consideration of the ensuing description and drawings.

The left side tubes are mirror-images of the respective right side tubes.

FIGS. 8, 9, 10, 11 and 12 show the different modes of tooth movements with the brackets and the molar tubes described in this specification.

DESCRIPTION OF THE INVENTION

The following describes the embodiments of the present invention as illustrated in FIGS. 1 to 7.

Figure 1:
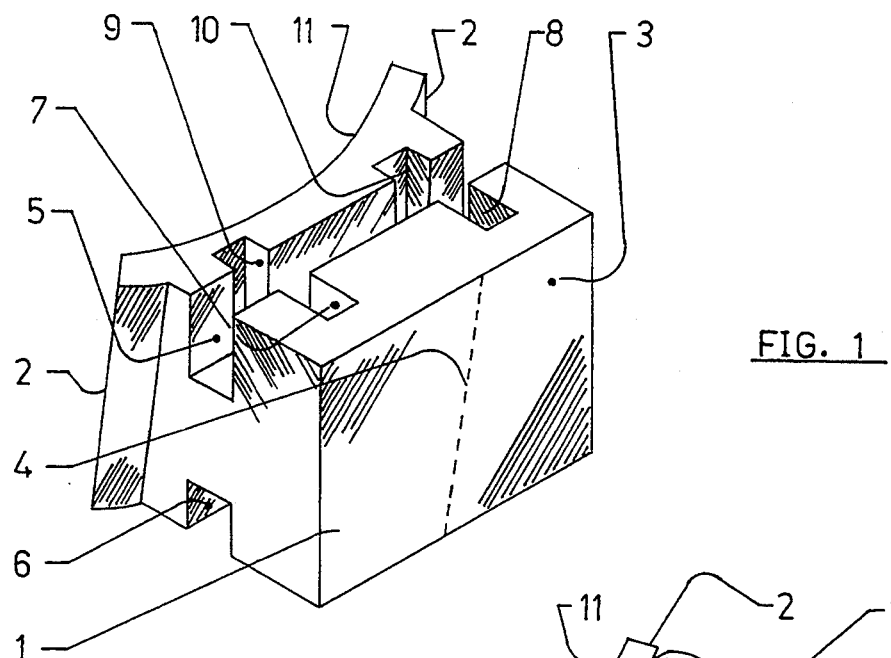
FIG. 1 is a perspective view of a bracket according to the present invention.
Figure 2:
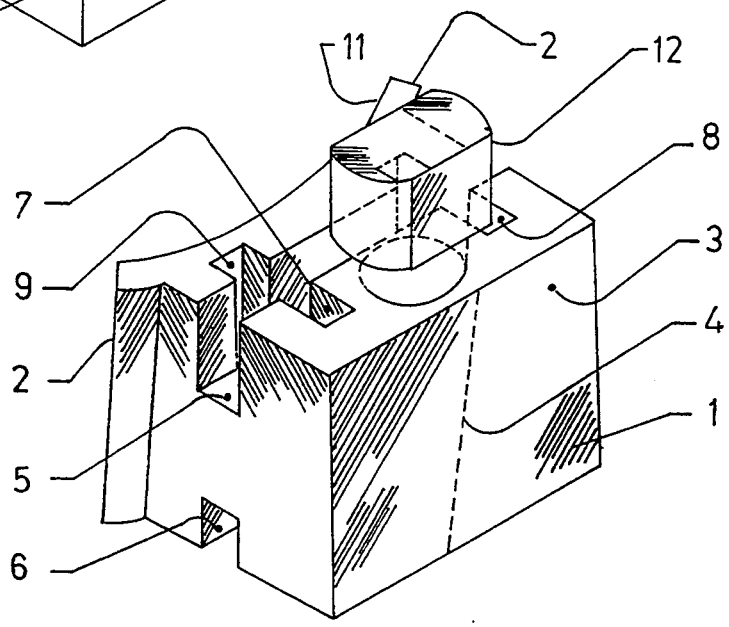
FIG. 2 is a perspective view of a bracket according to the present invention with a hook.
Figure 3:
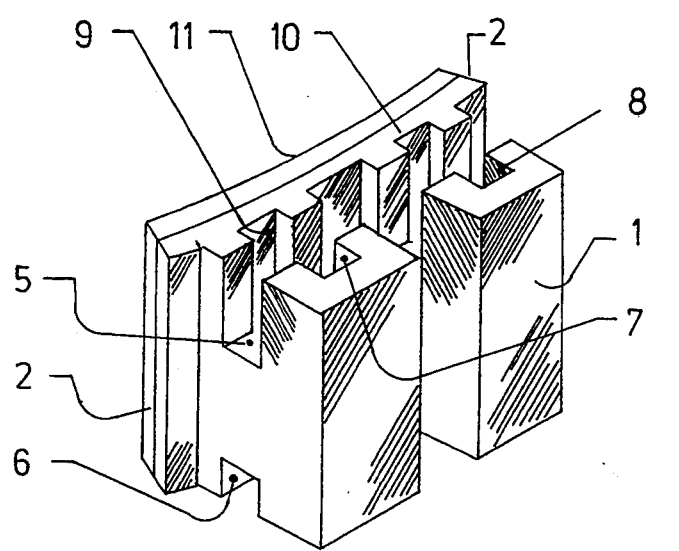
FIG. 3 is a perspective view of a modified version of the bracket of FIG. 1.
Figure 4:
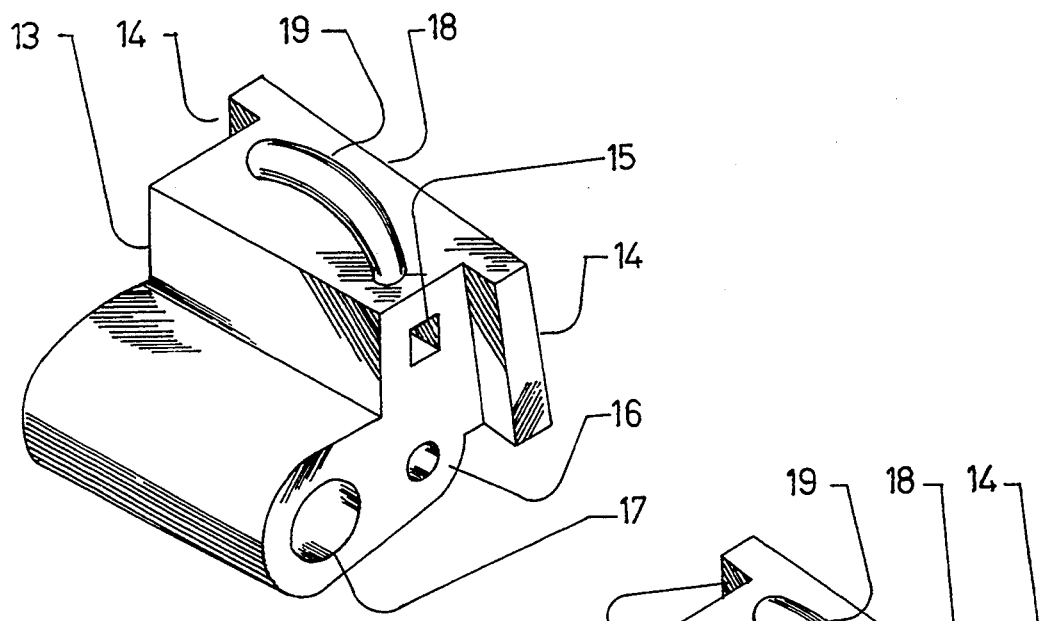
FIG. 4 is a perspective view of the upper right first molar tube of the present invention.
Figure 5:
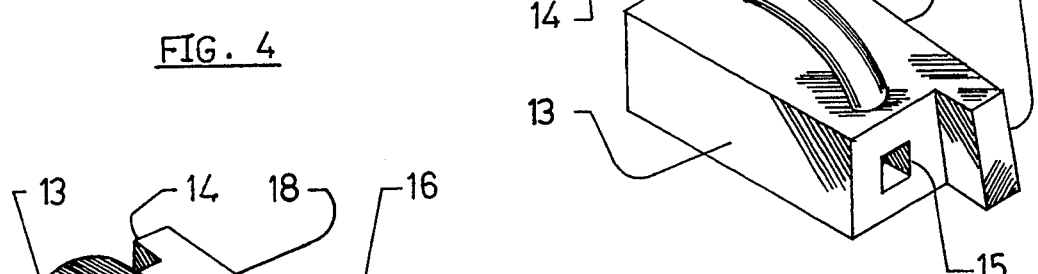
FIG. 5 is a perspective view of the upper right second molar tube of the present invention.
Figure 6:
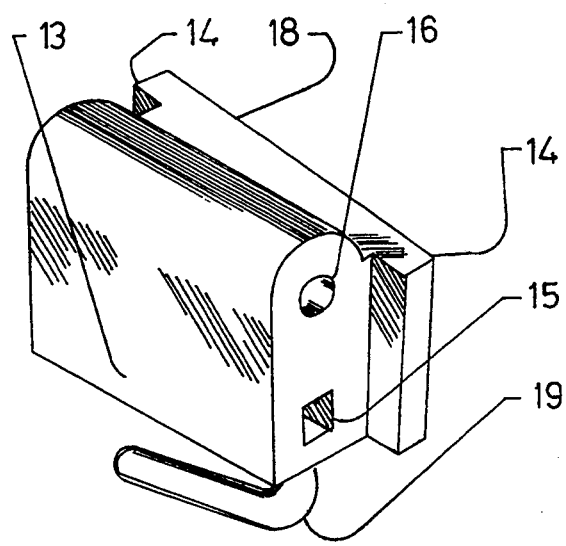
FIG. 6 is a perspective view of the lower right first molar tube of the present invention.
Figure 7:
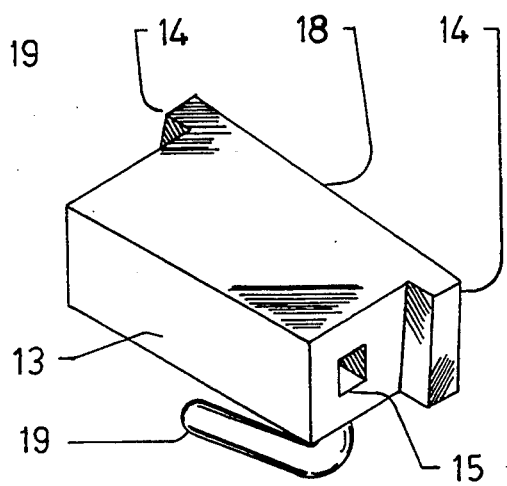
FIG. 7 is a perspective view of the lower right second molar tube of the present invention.
Figure 8:
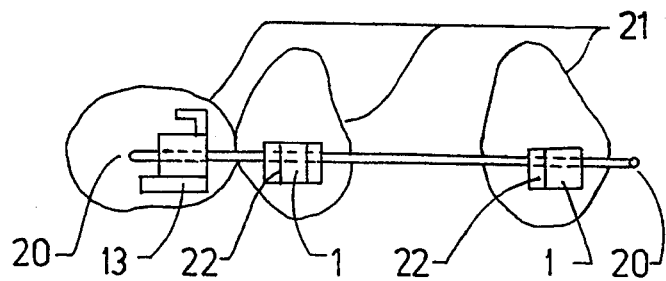

FIGS. 1, 2 and 3 show the bracket of the invention. The bracket includes two major portions, a body of the bracket 1 and a base 11. The body of the bracket can be of metal, plastic, ceramics or of any other permissible material. It carries a marking 4 on the labial/buccal surface for the tip angle and an identification marking 3 for each tooth. The tip angle is the angle between the long axis of the tooth with the true vertical. The tip angle marking 4 has to be in line with the long axis of the tooth when the bracket is fixed onto the tooth to get the correct inclination of the tooth at the end of the treatment. The common ideal tip angles for different teeth vary from 0 degree to 15 degrees. Flanges 2 are provided in metal brackets for welding a mesh pad or a metal band. A main horizontal rectangular arch wire slot 5 engages round and rectangular arch wires in ribbon-arch mode i.e. in a cross-section the height of the wire is more than the width. The slot 5 is in the gingival surface of the bracket i.e., it faces the gum margins of the tooth. The arch wire is secured to the slot 5 with an elastic module, a lock pin, or a ligature wire. A horizontal rectangular slot 6 in the incisal surface is used for tying ligature wires, elastic modules, and power chains. It can also be used for an additional round arch wire for the reinforcement of anchorage. Two vertical slots pass through the body of the bracket 1. The vertical slots are split into labial parts 7 & 8 and lingual parts 9 & 10 by the main horizontal rectangular arch wire slot 5 and the horizontal rectangular slot 6 in the incisal surface. These are used for lock pins and ligature wires. The labial slot 7/8 can also be used for uprighting springs if needed.

The base 11 of the bracket is contoured to fit the labial or lingual surface of the crown of a tooth. The base 11 is at an angle in the vertical direction with the main horizontal rectangular arch wire slot 5 to incorporate a torque angle. The torque angle is positive when the crown of the tooth is more buccal than the root of the tooth in relation to the vertical plane and it is negative when the root of the tooth is more buccal than the crown of the tooth. The upper central and the lateral incisors have positive torque angles whereas all the other teeth namely the upper canines, the first and the second premolars, the lower central and the lateral incisors, the canines, the first and the second premolars have negative torque angles. The torque angles for the different teeth vary from −17 degrees to +17 degrees.

The thickness of the base 11 varies. It is thinnest for all canine and premolar brackets. It is thickest for the upper lateral incisors and is of intermediate thickness for the upper central incisors and the lower central as well as the lateral incisor brackets.

A mesh is welded onto the base 11 of a metal bracket as a retentive means for direct bonding of the bracket onto the tooth or the bracket is welded onto a metal strip called a band which is cemented around the tooth. Plastic or ceramic brackets have retentive grooves in the base of the bracket.

A hook 12 is placed on the upper and the lower canine brackets for engaging elastics and power chains as shown in FIG. 2. Such a hook may be placed on the bracket of any tooth if so desired. It will be appreciated, however, that the bracket of the invention is not dependent upon having such a hook.

The bracket can also be as shown in FIG. 3. This bracket has a uniform base thickness for all the teeth and the base is not angulated in the vertical direction i.e., the tip angle and the torque angle are 0 degrees and the thickness of the base is not adjusted specifically for an individual tooth. Hence, this bracket does not have the identification marking 3, and the marking for the tip angle 4. The orthodontist has to incorporate bends in the arch wires to place the teeth precisely in their ideal positions. The working of the bracket, however, remains the same.

The edges of the brackets, while illustrated as being generally sharp, would be rounded or smoothened in actual practice to be comfortable in the mouth.

FIG. 4, 5, 6 and 7 show the molar tubes of the present invention. A molar tube of the invention includes a body 13 and a base 18. The body of the tube can be of metal or any other permissible material. A rectangular tube 15 is used for round and rectangular main arch wires in ribbon-arch mode for all the first and the second molars, upper and lower. A round tube 16 is used for an additional round arch wire to be used in some cases only. This tube is placed only in the upper and the lower first molar attachments, incisal to the rectangular tube. A bigger round tube 17 is used for the inner bow of a headgear. This tube is placed on the upper first molar attachments only.

The base of the molar tube 18 makes an angle with the sides of the molar tube 15 in the horizontal as well as in the vertical plane. The horizontal angulation is called the distal offset. It is placed to rotate the molar and maintain the molar in its proper position. The distal offset angle varies from 3 degree to 10 degrees. The vertical angulation is the torque angle. It is negative for all the first and the second molars. It varies from −10 degrees to −27 degrees. Flanges 14 are provided to facilitate welding of the molar tube to a metal band or a mesh pad.

Another embodiment of the tube presented would be a tube without a built-in distal offset and a torque angle.

A hook 19 is placed on the molar tube at the mesial end on the gingival surface. It is angulated away from the gums for an easy engagement of elastics and power chains. It will be appreciated, however, that the tube of the invention is not dependent upon having such a hook.

Different Modes of Tooth Movement

The working of the new orthodontic appliance presented here can be understood better by comparing it with the prior art appliances.

A tooth can be moved from one position to another by tipping and uprighting or by bodily movement.

The Begg Appliance moves teeth by tipping and uprighting. The Edgewise Appliance and its modifications move the teeth by bodily movements.

The Begg bracket allows free tipping but it cannot control the tipping and cannot upright/torque the tooth by itself. An uprighting/torquing spring is necessary for the purpose. Tooth movements with torquing and uprighting springs are not self-limiting. Also, as the bracket is not wide enough, control over tooth rotation is not adequate.

The Edgewise/modified Edgewise bracket has a horizontal slot which does not allow free tipping in mesiodistal direction which is a rapid movement and requires less force. Bodily movement of the teeth requires heavy forces causing discomfort to the patient. Also, an extraoral anchorage is required needing more patient cooperation.

The advantages of the present invention become evident when explained with the help of the diagrams and the numbers allotted to each part.

Figure 9:
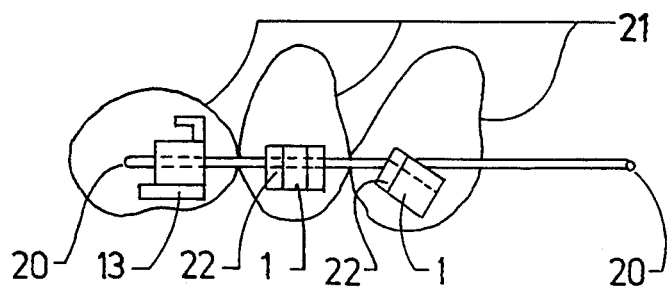
Figure 10:
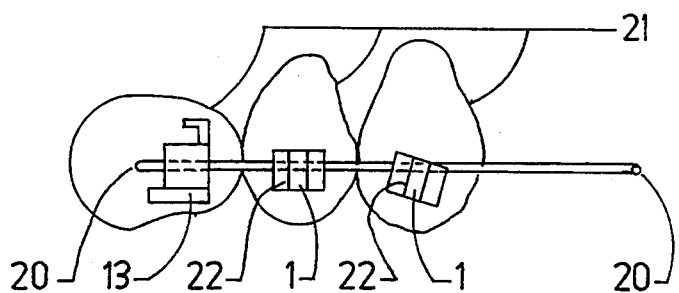
Figure 11:
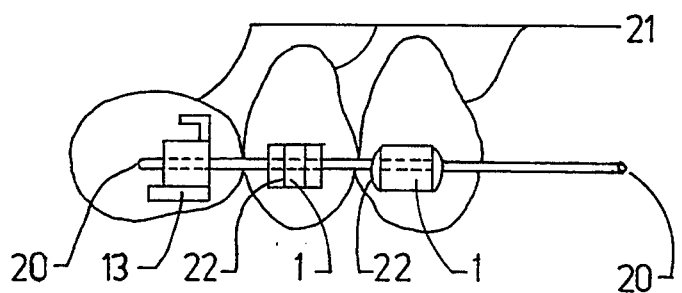

The new bracket which is presented here allows free tipping of the teeth 21 [FIG. 9], controlled tipping of the teeth 21 [FIG. 10] or bodily movement of the teeth 21 [FIG. 11] as required by the orthodontist.

The method of engagement of the arch wire 20 to the bracket 1 allows these selective movements.

If the arch wire 20 is tied with a ligature wire 22 to the distal slot 7/9 only, free distal tipping of the tooth 21 is obtained. If both the slots 7/9 and 8/10 are used or a single tie is used from the mesial to the distal then translatory or bodily movement is obtained. Controlled tipping results if the arch wire 20 is loosely tied to the bracket 1 as shown in FIG. 10.

Figure 12:
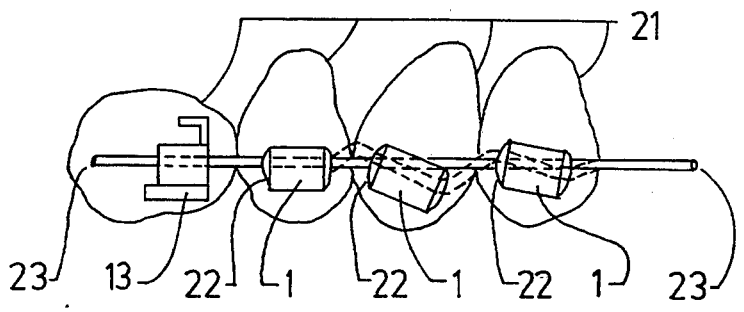

A tipped tooth 21 can be uprighted with the bracket 1 without using an uprighting spring by tying the wire to both the slots as shown in FIG. 12. A rectangular arch wire 23 is engaged in the last phase of treatment to position all the teeth 21 precisely with proper tip and torque angulations as well as the in and out relationships.

Depending on the malocclusion of the patient, complete orthodontic treatment is carried out in different stages. In the first stage, all the front teeth are brought into proper alignment, spaces are closed if present and the bite is opened by means of arch wires and elastics. In cases where teeth have been extracted for treatment purpose, the extraction spaces are closed in the second stage either by free tipping, controlled tipping or by translation. In the last stage, the teeth are placed in the desired positions by uprighting and torquing with rectangular arch wires. In cases where teeth have not been extracted they are settled in the desired positions by rectangular arch wires.

Although the description above contains many specificities, these should not be construed as limiting the scope of the invention but as merely providing illustrations of some of the presently preferred embodiments of this invention. For example, the bracket can have various shapes like round, square, oval, triangular, trapezoidal etc.; one or more vertical slots through the body of the bracket adjacent to the slots 7, 8, 9 and 10. The main horizontal rectangular arch wire slot 5 can be in the incisal surface and the other horizontal rectangular slot 6 can be in the gingival surface of the bracket. Thus the scope of the invention should be determined by the appended claims and their legal equivalents, rather than by the examples given.

What is claimed is:

1. An orthodontic appliance for applying forces to correct malocclusion of teeth, comprising:

a plurality of brackets for engaging arch wires in a predetermined manner; each of said brackets being attachable to teeth on the labial/buccal or the lingual surface of a crown; each of said brackets having a base contoured to fit a tooth surface and a body extending from said base; said body of each of said brackets having a labial/buccal/lingual surface, a gingival surface, an incisal surface, a mesial surface and a distal surface; said body of each of said brackets having a main horizontal rectangular arch wire slot in said gingival surface for engaging arch wires therein, said main horizontal rectangular arch wire slot being placed adjacent and parallel to said base of said bracket extending from said mesial surface to said distal surface, the depth of said main horizontal rectangular arch wire slot being more than its width; said body of each of said brackets having a horizontal rectangular slot in said incisal surface for engaging an additional arch wire, ligature wires, elastic modules, and power chains therein; said horizontal rectangular slot in said incisal surface being adjacent and parallel to said base of said bracket extending from said mesial surface to said distal surface; said body of each of said brackets having a pair of spaced apart vertical slots passing from said gingival surface to said incisal surface for lock pins and ligature wires;

a plurality of molar tubes for engaging arch wires in coordination with said brackets in a predetermined manner; each of said molar tubes being attachable to a molar tooth on the buccal/lingual surface thereof; each of said molar tubes having a base contoured to fit a tooth surface and a body extending from said base; said body of each of said molar tubes having a buccal/lingual surface, a gingival surface, an incisal surface, a mesial surface and a distal surface; said body of each of said molar tubes having a horizontal rectangular arch wire tube passing from said mesial surface to said distal surface adjacent and parallel to said base of said molar tube for engaging round and rectangular arch wires; the height of said horizontal rectangular arch wire tube of each of said molar tubes being more than its width.

2. An orthodontic appliance for applying forces to correct malocclusion of teeth, comprising:

a plurality of brackets for engaging arch wires in a predetermined manner; each of said brackets being attachable to teeth on the labial/buccal or the lingual surface of a crown; each of said brackets having a base contoured to fit a tooth surface and a body extending from said base; said body of each of said brackets having a labial/buccal/lingual surface, a gingival surface, an incisal surface, a mesial surface and a distal surface; said body of each of said brackets having a main horizontal rectangular arch wire slot in said gingival surface for engaging arch wires therein, said main horizontal rectangular arch wire slot being placed adjacent to said base of said bracket extending from said mesial surface to said distal surface, the depth of said main horizontal rectangular arch wire slot being more than its width, the sides of said main horizontal rectangular arch wire slot making an angle with said base of said bracket vertically to incorporate a torque angle specific for a particular tooth; said body of each of said brackets having an identification marking on said labial/buccal/lingual surface for identifying said bracket for the particular tooth; said body of each of said brackets having a marking for a tip angle specific for the particular tooth on said labial/buccal/lingual surface; said body of each of said brackets having a horizontal rectangular slot in said incisal surface for engaging an additional arch wire, ligature wires, elastic modules, and power chains therein; said horizontal rectangular slot in said incisal surface being adjacent to said base and extending from said mesial surface to said distal surface; said body of each of said brackets having a pair of spaced apart vertical slots passing from said gingival surface to said incisal surface for lock pins and ligature wires;

a plurality of molar tubes for engaging arch wires in coordination with said brackets in a predetermined manner; each of said molar tubes being attachable to a molar tooth on the buccal/lingual surface thereof; each of said molar tubes having a base contoured to fit a tooth surface and a body extending from said base; said body of each of said molar tubes having a buccal/lingual surface, a gingival surface, an incisal surface, a mesial surface and a distal surface; said body of each of said molar tubes having a horizontal rectangular arch wire tube passing from said mesial surface to said distal surface adjacent to said base of said molar tube for engaging round and rectangular arch wires therein, the height of said horizontal rectangular arch wire tube of each of said molar tubes being more than its width, the sides of said horizontal rectangular arch wire tube making an angle with said base of said molar tube vertically to incorporate a torque angle and horizontally to incorporate a distal off-set angle specific for a molar tooth.

3. The orthodontic appliance of claim 2, wherein the thickness of said base of each of said brackets vary to compensate for the variations in the shape, size, and relative positions of the teeth.

4. The orthodontic appliance of claim 3, wherein each of said molar tubes for the upper and the lower first molars being additionally provided with a round arch wire tube passing from said mesial surface to said distal surface near and parallel to said incisal surface spaced apart from said horizontal rectangular arch wire tube of said molar tube for engaging an additional arch wire.

5. The orthodontic appliance of claim 4, wherein each of said molar tubes for the upper first molars being additionally provided with a round tube for a headgear near and parallel to said buccal surface spaced apart from said round tube of said molar tube.

6. The orthodontic appliance of claim 5, wherein said body of each of said brackets for the upper and the lower canines being additionally provided with a hook on said gingival surface of said body for engaging elastics, said body of each of said molar tubes being additionally provided with a hook on said gingival surface near said mesial surface for engaging elastics.

7. The orthodontic appliance of claim 6, wherein the shape of said body of each of said brackets is selected from the group consisting of oval, square, rectangular, triangular, trapezoidal and circular.

* * * * *